United States Patent
Pollanz

[11] 3,943,774
[45] Mar. 16, 1976

[54] PRECISION TEMPERATURE CONTROL
[75] Inventor: Herwig Pollanz, Linkenheim, Germany
[73] Assignee: Gesellschaft fur Kernforschung m.b.H., Karlsruhe, Germany
[22] Filed: Aug. 2, 1974
[21] Appl. No.: 494,357

[30] Foreign Application Priority Data
Aug. 8, 1973 Germany............................ 2340055

[52] U.S. Cl................................ 73/432 R; 73/1 R
[51] Int. Cl.² ............................................ G01K 3/02
[58] Field of Search..... 73/1 R, 1 F, 343, 29, 432 R

[56] References Cited
UNITED STATES PATENTS
3,265,301  8/1966  Amdur et al............................ 73/29
3,521,865  7/1970  Kertzman............................ 73/29 X
3,532,270  10/1970  Schoen, Jr. ............................ 73/29

Primary Examiner—Donald O. Woodiel
Attorney, Agent, or Firm—Spencer & Kaye

[57] ABSTRACT

A method and apparatus for accurately holding a sample at a temperature in the range below 0°C by maintaining a constant temperature drop between an apparatus holding the sample and a coolant which is at a lower temperature, accompanied by inflow and outflow of small amounts of heat. The sample may be a measuring gas whose moisture content is to be set by establishing a given dew point temperature.

10 Claims, 4 Drawing Figures

DEW POINT TEMPERATURE, °C, AND
CORRESPONDING THEORETICAL WATER CONTENT, ppm

PRECISION TEMPERATURE CONTROL

BACKGROUND OF THE INVENTION

The present invention relates to a method for setting a given temperature in the temperature range below 0°C at a sample, particularly for setting a given moisture content in a gas at dew points in such temperature range, and to an apparatus for practicing the method.

In order to be able to perform certain types of experiments, such as, for example, sintering experiments with oxidic nuclear fuels in gas atmospheres having a defined low moisture content, it is necessary to employ devices which permit a defined and reproduceable setting of a moisture content for a measuring gas having a dew point in the range between −30° and −65°C. Studies of the properties of oxidic nuclear fuels such as $UO_2$ — $PuO_2$ for fast breeder reactors have demonstrated the necessity for being able to set a defined oxygen/metal ratio in the oxide on the basis of the moisture content of a hydrogen-containing measuring gas.

It is known to set given moisture contents in a gas, for example in air-conditioning systems by initially continually humidifying the gas and then extracting moisture therefrom, for example in a cooling trap, until the desired residual moisture content has been obtained.

It is also known to set given temperatures in the range below 0°C at a sample with the aid of cooling devices such as, for example, refrigerators, low temperature cryostats or Peltier cells and to control these cooling devices by means of thermostats.

Significant drawbacks of these known methods and apparatuses are the high costs for the apparatus involved, the relatively large space requirement, the relatively high operating costs, the large moisture and ice quantities that must be converted, and the corresponding large structural size required for the humidifying and freezing devices.

SUMMARY OF THE INVENTION

It is therefore an object of the present invention to permit the setting of a given temperature at a sample, and thus the establishment of a desired gas moisture content, in the range of 0°C to about −90°C with very low expenditure for the apparatus and with low energy requirement.

This and other objects are accomplished, according to the present invention, by maintaining, between an apparatus for holding the sample and a coolant which is at a lower temperature level, a constant temperature drop, accompanied by inflow and outflow of small amounts of heat.

More specifically, in accordance with the present invention, at low temperatures and with small quantities of heat flowing in and out, a stationary temperature drop is maintained between a coolant, such as liquid nitrogen for example, and a gaseous medium, such as a measuring gas, whose moisture content is to be set by a given dew point temperature in order to achieve a constant temperature such as the dew point temperature which can be varied between the lowest temperature i.e. the temperature of the coolant and the highest temperature i.e. the inlet temperature of the measuring gas.

It has here been found to be particularly advantageous to conduct a gas which is laden with moisture over a surface which is kept at a given temperature so that the gas reaches a temperature below the dew point temperature, whereby part of the moisture in the gas is deposited on the surface in the form of a condensate and is there converted to a layer of ice, after that the measuring gas being conducted over this ice layer so that, initially, the relative humidity of the gas is less than 100% and, after a sufficiently long period of dwell in the region of the ice layer, it reaches a given constant percentage which is near 100% of the saturation vapor pressure which corresponds to the given temperature.

A particularly simple device for setting a given moisture content in a gas includes an adjustable cooling trap disposed in a first insulated vessel which is in turn disposed within a second insulated vessel, the second insulated vessel being partially filled with a liquid coolant whose level is kept constant during operation by means of a level controller, the first insulating vessel being immersed with its lower end into the liquid coolant and a thermocouple for measuring the dew point temperature being disposed at the point of gas flow direction reversal in the cooling trap. A thin-walled heat conducting tube of a material with good heat-conducting properties, such as copper for example, is inserted into the first insulating vessel and a thermal insulation, for example a foamed plastic, is disposed between the inner wall of the first insulating vessel and the heat conducting tube.

The advantages obtained with the present invention are, in particular, that due to the small amounts of heat flowing in and out, it is possible to set and maintain, with simple means, a constant temperature drop between a coolant, e.g. liquid nitrogen, and the sample, and that it is only necessary to provide simple devices which do not take up much space and whose operating costs are extremely low.

DESCRIPTION OF THE PREFERRED EMBODIMENTS

Figure 1:
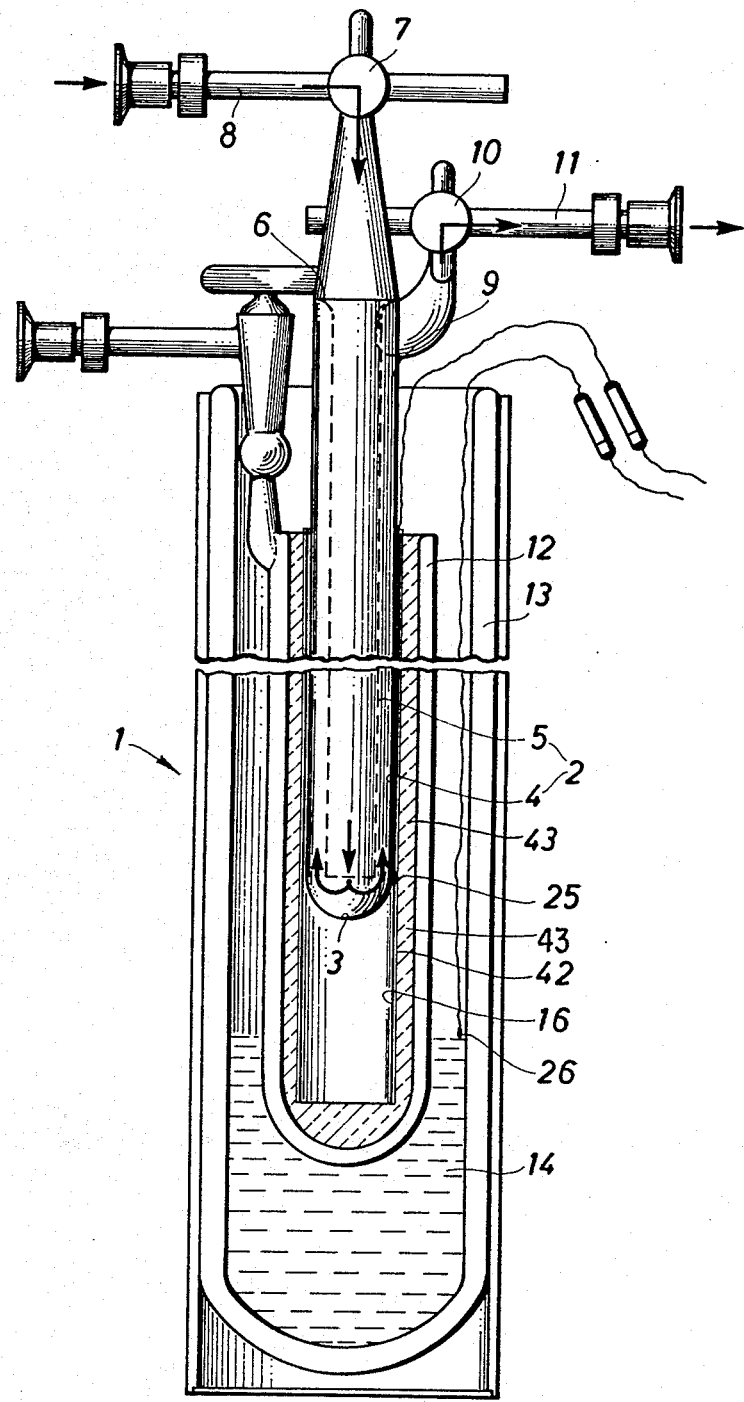
FIG. 1 is an elevational cross-sectional view of a humidifying cell in accordance with the invention.

FIG. 1 shows a preferred embodiment of a humidification cell 1 according to the invention, which substantially includes a cooling trap 2 formed by a tubular, elongate vessel 4 whose lower end 3 is closed and which has a circular cross section, and a tube 5 concentrically disposed in vessel 4 and hermetically sealed, at its upper end 6, to the inner wall of vessel 4. Tube 5 is connected, via an inlet valve 7, with a gas inlet line 8, and the annular chamber 9 formed between vessel 4 and tube 5 is connected to a gas outlet line 11 via an outlet valve 10.

The cooling trap 2 is disposed in a first insulated vessel 12 and the latter is in turn disposed in a second insulated vessel 13. The second insulated vessel 13 is filled in part with a liquid coolant 14, for example liquid nitrogen, whose level is kept constant on a predetermined value during operation by means of a level control 15. The first insulated vessel 12 enters with its lower end into the liquid coolant 14. The cooling trap 2 is displaceably mounted in a thin-walled copper tube 16 for a good axial heat conduction. The copper tube 16 extends over the entire length of the first insulating vessel 12, is wrapped in aluminum foil 42 on its outside and insulated against the interior wall of the first insulated vessel 12 by means of a heat insulating substance 43, which may be, for example, a foamed plastic.

Vessels 12 and 13 may each be, for example, a double walled vessel having the region between the walls under vacuum.

The humidification cell 1 may be used, for example, to set a given moisture content in a gas at dew points in the temperature range below 0°C. A few auxiliary instruments are required in this case, and these may be arranged as shown in FIG. 2.

Figure 2:
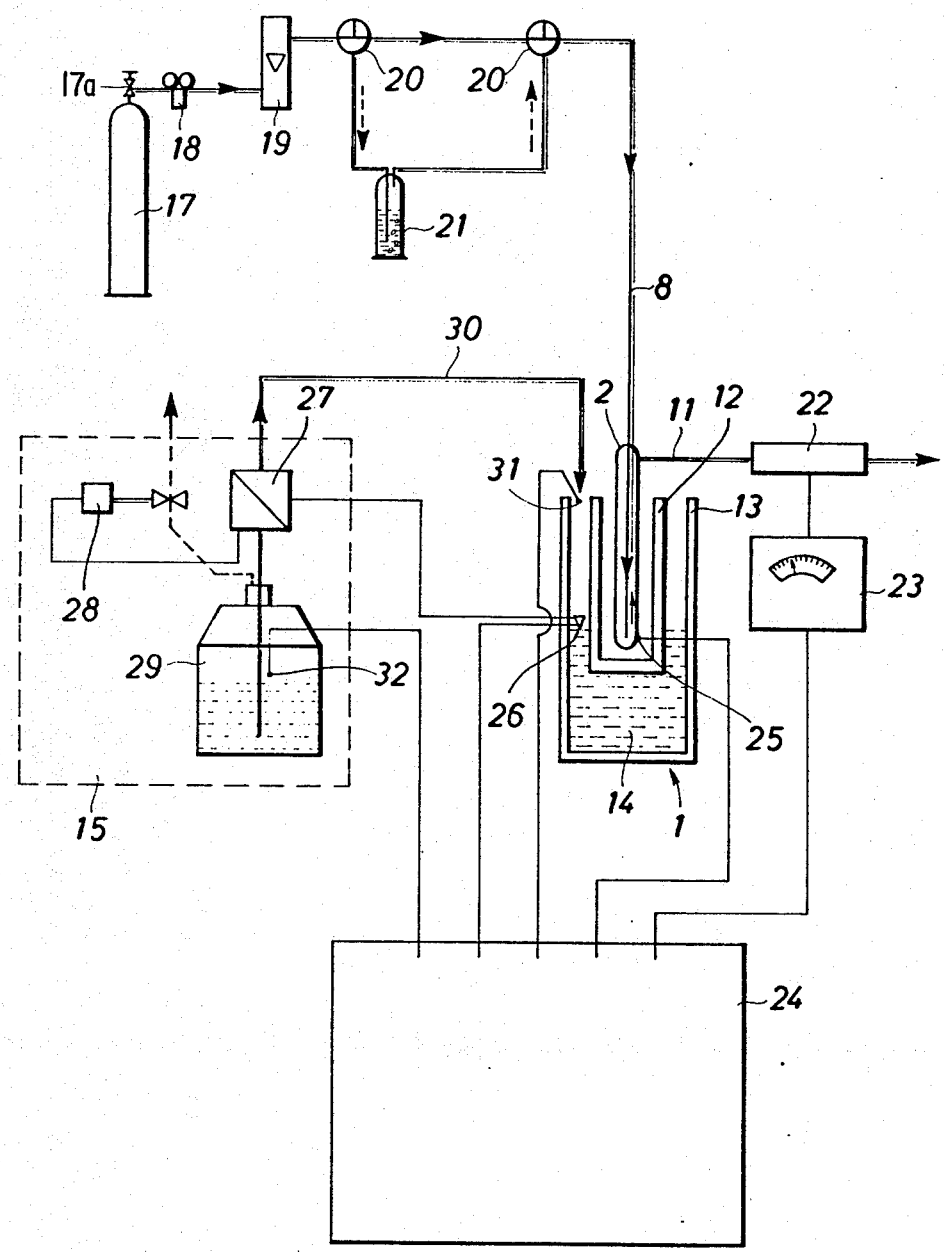
FIG. 2 is a diagrammatic view of a device according to the invention for setting a given moisture content in a gas.

Referring now specifically to FIG. 2, dry measuring gas, e.g. helium, is obtained from a bottle 17 and is conducted, in order to set a constant preliminary gas pressure, through a pressure control valve 18 and a gas flow meter 19, and, via a gas inlet line 8 to the cooling trap 2. A bypass which can be connected into the gas inlet line 8 via three-way valves 20 includes a device 21 for humidifying the gas. The cooling trap 2 can thus be fed via inlet valve 7 (FIG. 1) either with dry measuring gas or with gas charged with $H_2O$. A standard, known analysis cell 22 for measuring the moisture content of the measuring gas coming from the cooling trap is connected to the gas outlet line 11. The moisture content values obtained in the analysis cell 22 are indicated, after appropriate amplification, in an indicator 23 and are recorded by a multiple-input recorder 24.

The dew point temperature of the measuring gas is measured at the point of gas flow direction reversal in the cooling trap 2 by means of a thermocouple 25 which is fastened at the lower end 3 of the cooling trap 2, either at the outside or the inside of vessel 4.

The level of liquid coolant 14 is controlled by a thermocouple 26 whose output voltage is supplied to an electronic control device 27 in a level control unit 15 to control a magnetically-operated valve 28 of a reservoir 29 for liquid coolant, e.g. nitrogen, which valve connects the vapor space at the top of reservoirs 29 with the atmosphere. Magnetic valve 28 is thus held open as long as the tip of the thermocouple 26 is wetted by the coolant 14 disposed in the second insulated vessel 13. If the wetting is interrupted because the coolant level drops, a sudden change in temperature occurs at thermocouple 26 which actuates, as a change in voltage, a switching pulse for closing valve 28. Thus a pressure increase occurs in reservoir 29 because of continued evaporation of coolant so that liquid coolant is conducted into the second insulated vessel 13 through an insulated line 30. The filling process is monitored by a thermocouple 31 disposed in the inlet opening to vessel 13. In the lower third of the reservoir 29 a thermocouple 32 is disposed to monitor the fill level thereof and emit a warning signal when a given minimum fill level is no longer being maintained.

The measured voltages produced by thermocouples 25, 26, 31 and 32 are recorded by multiple-input recorder 24 as are the moisture values measured by analysis cell 22.

At the beginning of the operation, about 20 l/h to 50 l/h of gas moistened with water — this gas or the measuring gas being, for example, highly pure helium, helium containing 5% hydrogen, highly pure argon, or argon containing 5% hydrogen — is conducted through the cooling trap 2. The gas is moistened by passage through humidifying device 21. An ice layer thus forms on the inner walls of tube 5. After about 1 hour the bypass can be switched off and dry measuring gas can be used.

Figure 3:
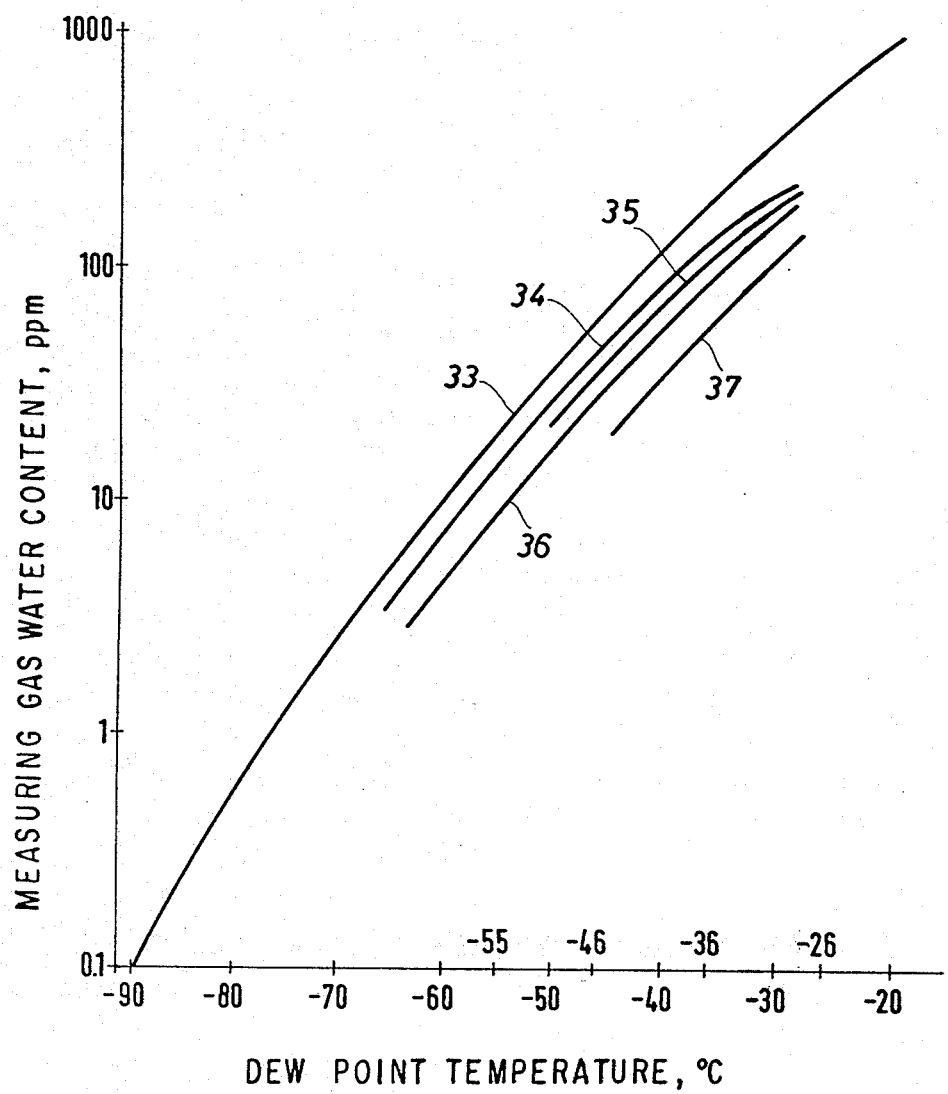
FIG. 3 is a diagram showing moisture contents as a function of dew point temperatures, used in explaining the operation of the invention.

FIG. 3 shows the water content of the measuring gas in volume parts per million in dependence on the dew point temperature. Curve 33 constitutes the theoretical saturation curve, while curve 34 is the saturation curve determined by the apparatus of the invention. The apparently inherent difference between these two curves can be reproduced and depends substantially on the arrangement of the thermocouple 25 provided to measure the dew point temperature. It is here a prerequisite that the analysis cell 22 be accurately calibrated to handle 100 normal liters per hours, on which flow curve 34 is based. Curves 35, 36 and 37 are the result of measured values obtained with flowthroughs of 75, 50 and 20 normal liters per hour, respectively, and a measuring gas of the composition of highly pure helium with 5% hydrogen.

Curves 35, 36 and 37 depict apparent moisture contents below saturation. The deviations from the saturation curve 34 are a result of the flowthrough dependence of the measured values on the analysis cell 22 employed.

Figure 4:
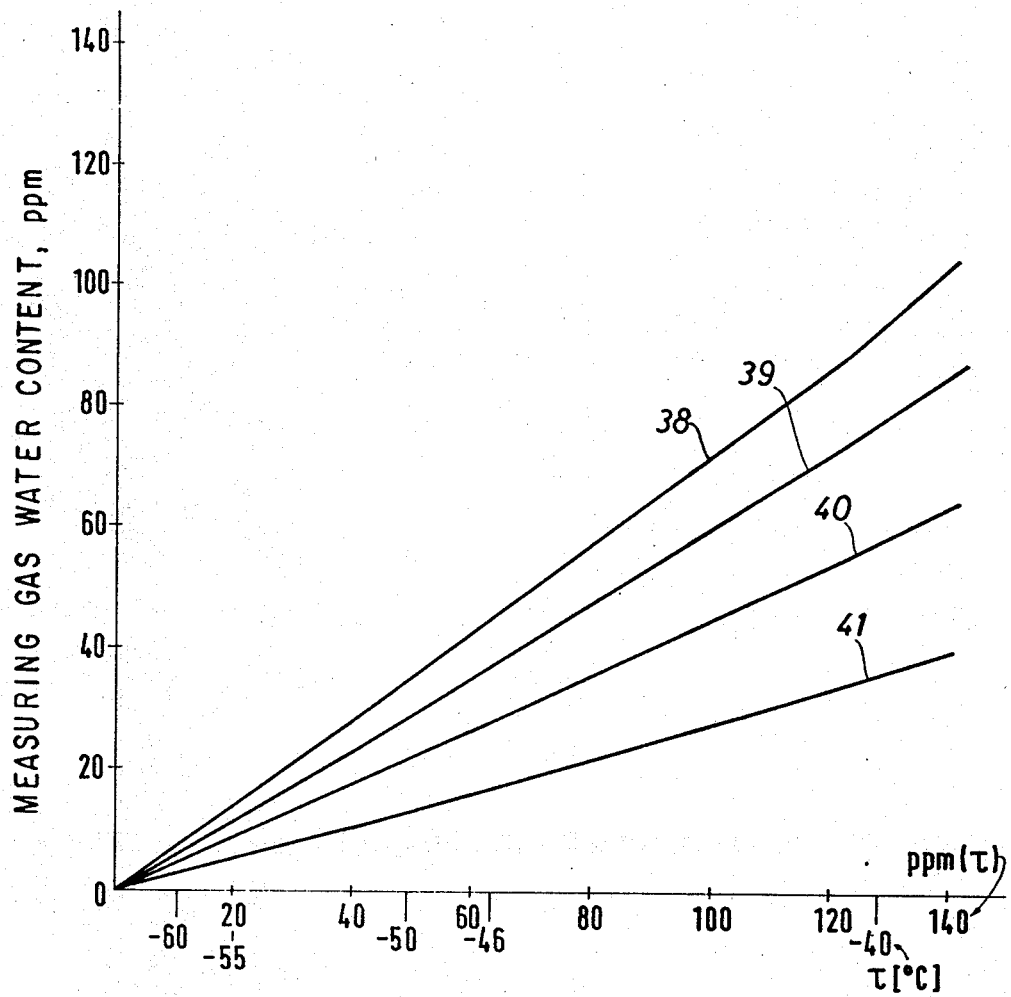
FIG. 4 is a diagram showing the dependence of the actual and apparent moisture content on flow-through in systems according to the invention.

FIG. 4 shows, to a linear scale, the water content of the measuring gas in volume parts per million in dependence on the dew point temperature. The theoretical corresponding water content, in volume parts per million, is also indicated linearly along the dew point axis. The associated theoretical dew points are evident from curve 33 of FIG. 3.

Curve 38 shows the actual water content indicated by analysis cell 22 for a flowthrough of 100 NL/h. Curves 39, 40 and 41 show apparent water content values measured by analysis cell 22 for the highly pure helium containing 5% $H_2$ which was employed as the measuring gas at flowthroughs of 75, 50 and 20 NL/h, which do not correspond to the calibration of the analysis cell. By vertical projection of the apparent measured value from curve 39, 40 or 41 on curve 38, the actual water content can be determined from the ordinate.

In order to maintain a constant temperature drop between the coolant 14, having a constant temperature — e.g. liquid nitrogen at its boiling point — and the measuring gas flowing into the cooling trap 2 at its upper end 6 having a constant temperature all parameters which influence the heat balance are kept constant.

Such parameters are the rate of flow of the measuring gas, its inlet temperature, the immersion depth of the first insulating vessel 12 into the coolant 14 and finally the uncoated length of the cooling trap 2 and of the heat conducting copper tube 16 which stand out at the upper end of the second insulating vessel 13.

Within this constant temperature drop any constant temperature at the point of gas flow direction reversal in the cooling trap can be set by axial adjustment of the cooling trap.

Other methods for achieving a given constant temperature at the point of gas flow direction reversal are the variation of the level of the coolant 14, the variation of the constant temperature by changing the type of coolant or an additional electrical heating of the heat conduction copper tube 16 at its upper end.

It will be understood that the above description of the present invention is susceptible to various modifications, changes and adaptations, and the same are intended to be comprehended within the meaning and range of equivalents of the appended claims.

I claim:

1. Apparatus for giving a gas a predetermined moisture content at a dew point in a temperature range below 0°C, comprising: a first insulated vessel; a cooling trap disposed in said first insulated vessel; a second insulated vessel in which the first insulated vessel is disposed; a mass of liquid coolant partially filling said second insulated vessel; level control means operatively arranged for maintaining said coolant above a predetermined level in said second vessel, said first insulated vessel being immersed with its lower end into the liquid coolant; means for causing such gas to flow through said cooling trap; and a first thermocouple disposed at the point of gas flow direction reversal in said cooling trap for measuring the dew point temperature of the gas.

2. Apparatus as defined in claim 1 wherein said cooling trap comprises a tubular, elongate vessel having a circular cross section and closed at its lower end; a tube concentrically disposed within said elongate vessel, said tube being open at its lower end and being gastightly connected to said elongate vessel at its upper end, with the lower ends of said tube and said elongate vessel defining an annular gap; a gas inlet line connected at the upper end of said tube to be in communication with the interior of said tube; an inlet valve disposed in said inlet line; a gas discharge line connected to be in communication with said annular gap between said elongate vessel and said tube; and an outlet valve disposed in said discharge line.

3. Apparatus as defined in claim 2 wherein said cooling trap further comprises a thin-walled tube of a material with good heat-conducting properties inserted into said first insulated vessel; and a body of thermal insulation disposed between the inner wall of said first insulated vessel and said thin-walled tube.

4. Apparatus as defined in claim 3 wherein said thin-walled tube is formed of a rolled sheet metal whose ends overlap one another and form a parting line which extends parallel to the axial direction of said thin-walled tube.

5. Apparatus as defined in claim 3 further comprising a layer of aluminum foil wound around the outer surface of said thin-walled tube.

6. Apparatus as defined in claim 1 wherein said level control means comprise a second thermocouple disposed in the annular space between said first insulated vessel and said second insulated vessel for monitoring the level of said liquid coolant.

7. Apparatus as defined in claim 6 wherein said level control means comprises: a reservoir containing a mass of such liquid coolant; a ventilating line communicating with the top of said reservoir; a magnetically operated valve disposed in said ventilating line; and an electronic control device connected to control delivery of liquid coolant from said reservoir to said second insulated vessel; said second thermocouple being connected to control the operation of said control device.

8. Apparatus as defined in claim 7 further comprising: a gas bottle containing such gas and having a supply outlet connected to said gas inlet line; a low pressure control valve and a gas flowthrough monitor connected between said bottle and said gas inlet line; means for charging the gas with water vapor; and switching means for selectively placing said water vapor charging means in the gas flow path between said bottle and said gas inlet line.

9. Apparatus as defined in claim 8 further comprising: an analysis cell disposed in said gas outlet line for measuring the moisture content of the gas leaving said coolant trap; and an indicator provided with an amplifier connected to the output of said analysis cell.

10. Apparatus as defined in claim 9 further comprising: a third thermocouple disposed for monitoring the supply of coolant to said second insulated vessel; a fourth thermocouple disposed for monitoring the level of liquid coolant in said reservoir; and a multiple-input recorder connected to record the measuring signals produced by said thermocouples and said analysis cell.

* * * * *